United States Patent [19]

Mausner

[11] Patent Number: 5,460,808
[45] Date of Patent: Oct. 24, 1995

[54] MASCARA COMPOSITION

[75] Inventor: Jack Mausner, New York, N.Y.

[73] Assignee: Chanel, Inc., New York, N.Y.

[21] Appl. No.: 192,192

[22] Filed: Feb. 4, 1994

Related U.S. Application Data

[63] Continuation of Ser. No. 981,947, Nov. 24, 1992, abandoned, which is a continuation of Ser. No. 701,464, May 15, 1991, abandoned.

[51] Int. Cl.$^6$ .................................. A61K 7/02; A61K 7/06
[52] U.S. Cl. ............................................. 424/70.7; 424/63
[58] Field of Search .................................. 424/401, 70, 63, 424/64, 70.7

[56]  References Cited

U.S. PATENT DOCUMENTS

| | | | |
|---|---|---|---|
| 3,697,643 | 10/1972 | Shepherd | 424/63 |
| 3,864,275 | 2/1975 | Kan et al. | 424/497 |
| 3,911,105 | 10/1975 | Papantoniou | 424/64 |
| 3,966,398 | 6/1976 | Vanlerberghe et al. | 424/70 |
| 4,125,549 | 11/1978 | Coopersmith | 424/64 |
| 4,247,411 | 1/1981 | Vanlerberghe et al. | 424/59 |
| 4,369,037 | 11/1983 | Matsunaja | 424/70 |
| 4,423,031 | 12/1983 | Murui | 424/63 |
| 4,440,295 | 8/1983 | Ootsu et al. | 264/250 |
| 4,460,371 | 7/1984 | Abber | 424/448 |
| 4,481,186 | 11/1984 | Deckner | 424/59 |
| 4,549,990 | 10/1985 | Seguin et al. | 552/545 |
| 4,608,392 | 8/1986 | Jacquet | 424/70 |
| 4,752,496 | 6/1989 | Fellows | 424/64 |
| 4,758,599 | 7/1988 | Minetti | 424/73 |
| 4,820,510 | 4/1989 | Arraudeau | 424/63 |
| 4,883,659 | 11/1989 | Goodman et al. | 424/70 |
| 4,925,667 | 5/1990 | Fellows | 424/64 |
| 4,927,952 | 5/1990 | Gueyne et al. | 556/419 |
| 4,952,560 | 8/1990 | Kigasawa et al. | 514/773 |
| 4,980,155 | 12/1990 | Shah | 424/63 |
| 4,988,502 | 1/1991 | Ounanian | 424/64 |
| 5,034,226 | 7/1991 | Beck | 424/74 |
| 5,037,803 | 8/1991 | Gueyne et al. | 424/59 |
| 5,053,220 | 10/1991 | Arraudeau | 424/63 |
| 5,053,221 | 10/1991 | Robertson | 424/63 |
| 5,061,481 | 10/1991 | Suzuki | 424/70 |
| 5,116,607 | 5/1992 | Jones | 424/70 |
| 5,182,103 | 1/1993 | Hakane | 424/78.03 |

*Primary Examiner*—Thurman K. Page
*Assistant Examiner*—Sally Gardner
*Attorney, Agent, or Firm*—Merchant, Gould, Smith, Edell, Welter & Schmidt

[57]  ABSTRACT

A mascara composition comprises: water, and emulsified and dispersed in the water, a protein component, a vegetable wax component, and a vitamin component. The protein component, the vegetable wax component, and the vitamin component are each present in cosmetically effective quantities. The protein component can be silk powder and keratin, the vegetable wax component can be rose wax and jasmine wax, and the vitamin component can be ascorbyl palmitate, tocopheryl acetate, and panthenol. The composition can further comprise an antioxidant component, a preservative component, an emulsifier component, a solvent component, a thickener component, a hydrophobic/waxy component, and at least one colorant. The mascara composition of the present invention is effective in significantly lengthening and thickening the eyelashes of the wearer and is significantly long lasting, water resistant, and safe for wearers. It further improves significantly the condition of lashes, making them softer, smoother, and more pliable. The formula is also soothing, calming, and anti-irritant.

2 Claims, No Drawings

MASCARA COMPOSITION

This is a continuation of application Ser. No. 07/981,947, filed Nov. 24, 1992, which was abandoned upon the filing thereof, which is a continuation U.S. Ser. No. 701,464, filed May 15, 1991, now abandoned the contents of which are hereby incorporated by reference.

BACKGROUND

This application is directed to mascara compositions.

Mascara is a commonly used cosmetic. It is applied to the eyelashes to enhance their appearance. An effective mascara composition must appear to thicken and lengthen the lashes, must be easy to apply and remove, must apply evenly, not smudge or flake, and be long lasting and water resistant after application. It also must be readily removable with conventional eye makeup removers, must not cause allergic reactions, and must be safe for contact lens wearers.

Although a great number of mascara compositions exist, there is a need for a mascara composition that is longer lasting, easy to apply, water resistant, safe, effective in thickening and lengthening the lashes and effective in imparting an attractive appearance to the lashes of the wearer. There is also a need for a mascara composition that provides care for and improves the actual condition of the eyelashes by making them softer, smoother, and more pliable.

SUMMARY

A mascara composition according to the present invention meets these needs. The mascara composition of the present invention is longer lasting, water resistant, easy to apply, and effective in lengthening and thickening the eyelashes of the wearer. It significantly improves the condition of the lashes by making them softer, smoother, and more pliable. It is safe for contact lens wearers and readily removable with conventional eye makeup.

The mascara composition of the present invention comprises: water, and emulsified and dispersed in the water:

(1) a protein component;

(2) a vegetable wax component; and (3) a vitamin component.

The protein component, the vegetable wax component, and the vitamin component are each present in cosmetically effective quantities.

The protein component can comprise at least one protein selected from the group consisting of silk powder and keratin. Preferably, the protein component comprises both silk powder and keratin; most preferably, the silk powder comprises from about 0.5% to about 5% of the composition and the keratin comprises from about 0.5% to about 5% of the composition.

The vegetable wax component comprises at least one vegetable wax selected from the group consisting of rose wax and jasmine wax. Preferably, the vegetable wax component comprises both rose wax and jasmine wax. Most preferably, the rose wax comprises from about 0.1% to about 3% of the composition and the jasmine wax comprises from about 0.1% to about 3% of the composition.

The vitamin component comprises at least one vitamin selected from the group consisting of fatty acid esters of ascorbic acid and their derivatives, tocopheryl esters and their derivatives, and panthenol and its derivatives.

The fatty acid esters of ascorbic acid can be selected from the group consisting of ascorbyl palmitate, ascorbyl myristate, ascorbyl stearate, and mixtures thereof; preferably, the fatty acid ester of ascorbic acid is ascorbyl palmitate. The tocopheryl esters and their derivatives can be selected from the group consisting of tocopheryl acetate, tocopheryl propionate, tocopheryl butyrate, and mixtures thereof; preferably, the tocopheryl ester is tocopheryl acetate.

Preferably, the vitamin component comprises ascorbyl palmitate, tocopheryl acetate, and panthenol. Most preferably, the ascorbyl palmitate comprises from about 0.05% to about 0.25% of the composition, the tocopheryl acetate comprises from about 0.1% to about 0.3% of the composition, and the panthenol comprises from about 0.01% to about 0.25% of the composition.

In addition to the protein component, the vegetable wax component, and the vitamin component, designated the cosmetic components, the mascara composition of the present invention can further comprise additional ancillary components. These ancillary components can include (1) an antioxidant component; (2) a preservative component; (3) an emulsifier component; (4) a solvent component; (5) a thickener component; (6) a hydrophobic/waxy component; and (7) colorant. Most preferably, the composition of the present invention comprises all of these ancillary components in addition to the cosmetic components.

The antioxidant component can be a mixture of 70% propylene glycol, 20% propyl gallate, and 10% citric acid, the mixture preferably being present in a quantity comprising from about 0.05% to about 0.25% of the composition.

The preservative component can comprise at least one preservative selected from the group consisting of:

(1) a complex consisting essentially of phenoxyethanol, methylparaben, ethylparaben, propylparaben, and butylparaben;

(2) propylparaben; and (3) sodium dehydroacetate.

Preferably, the preservative component comprises all of these preservatives; most preferably, the complex consisting essentially of phenoxyethanol, methylparaben, ethylparaben, propylparaben, and butylparaben comprises from about 0.4% to about 1.25% of the composition, propylparaben comprises from about 0.02% to about 0.08% of the composition, and sodium dehydroacetate comprises from about 0.01% to about 0.25% of the composition.

The emulsifier component can comprise at least one emulsifier selected from the group consisting of triethanolamine and a glyceryl ester. The glyceryl ester can be selected from the group consisting of glyceryl stearate, glyceryl palmitate, glyceryl arachidate, and mixtures thereof; preferably, the glyceryl ester is glyceryl stearate. Preferably, the emulsifier component contains both triethanolamine and glyceryl stearate. Most preferably, the triethanolamine comprises from about 2% to about 5% of the composition and the glyceryl stearate comprises from about 1% to about 4% of the composition.

The solvent component can be selected from the group consisting of ethylene glycol, propylene glycol, butylene glycol, and mixtures thereof. Preferably, the solvent component is propylene glycol. Most preferably, the propylene glycol comprises from about 0.4% to about 2.25% of the composition.

The thickener component can comprise at least one thickener selected from the group consisting of acacia and hydroxyethylcellulose. Preferably, the thickener component contains both acacia and hydroxyethylcellulose. Most preferably, the acacia comprises from about 3% to about 8% of the composition and the hydroxyethylcellulose comprises from about 0.1% to about 2% of the composition.

The hydrophobic/waxy component can comprise at least one ingredient selected from the group consisting of long-chain fatty acids, beeswax, carnauba, and paraffin. The long-chain fatty acids can be selected from the group consisting of palmitic acid, stearic acid, arachidic acid, and mixtures thereof. Preferably, the long-chain fatty acid is stearic acid. Preferably, the hydrophobic/waxy component comprises long-chain fatty acids, beeswax, carnauba, and paraffin. Most preferably, the stearic acid comprises from about 3% to about 8% of the composition, the beeswax comprises from about 4% to about 8% of the composition, the carnauba comprises from about 1% to about 4% of the composition, and the paraffin comprises from about 4% to about 10% of the composition.

The colorant can comprise from about 4% to about 8% of the composition.

A preferred mascara composition according to the present invention comprises: water, and emulsified and dispersed in the water:

(1) about 2% to about 5% of triethanolamine;
(2) about 0.4% to about 2.25% of propylene glycol;
(3) about 0.4% to about 1.25% of a complex consisting essentially of phenoxyethanol, methylparaben, ethylparaben, propylparaben, and butylparaben;
(4) about 0.01% to about 0.25% of sodium dehydroacetate;
(5) about 0.01% to about 0.25% of panthenol;
(6) about 3% to about 8% of acacia;
(7) about 0.1% to about 2% of hydroxyethylcellulose;
(8) about 0.5% to about 5% of silk powder;
(9) about 4% to about 8% of colorant;
(10) about 0.5% to about 5% of keratin;
(11) about 0.5% to about 2.5% of ascorbyl palmitate;
(12) about 4% to about 8% of beeswax;
(13) about 3% to about 8% of stearic acid;
(14) about 1% to about 4% of glyceryl stearate;
(15) about 1% to about 4% of carnauba;
(16) about 4% to about 10% of paraffin;
(17) about 0.05% to about 0.25% of a mixture of 70% propylene glycol, 20% propyl gallate, and 10% citric acid;
(18) about 0.2% to about 0.8% of propylparaben;
(19) about 0.1% to about 0.3% of tocopheryl acetate;
(20) about 0.1% to about 3% of jasmine wax; and
(21) about 0.1% to about 3% of rose wax.

DESCRIPTION

A new combination of ingredients produces a mascara that is long-lasting, water-resistant, and effective in thickening and lengthening the lashes, plus importantly improving the condition of the lashes. The mascara of the present invention comprises an aqueous base in which cosmetic components are emulsified and dispersed. Optimally, the mascara can also comprise ancillary components, such as an antioxidant component, a preservative component, an emulsifier component, a solvent component, a thickener component, a hydrophobic/waxy component, and a colorant.

The ingredients are dispersed in an emulsified composition by the method of preparation discussed below. "Dispersal" refers to any process by which the ingredients are uniformly distributed in the emulsified base, and includes dissolving, emulsifying, and forming a colloidal suspension.

I. NATURE AND PROPORTION OF INGREDIENTS OF THE MASCARA COMPOSITION

A. The Cosmetic Components

The cosmetic components include: (1) a protein component; (2) a vegetable wax component; and (3) a vitamin component. Each of these components contributes to the improved properties of the mascara composition of the present invention and the condition of the lashes to which the composition is applied and is present in a cosmetically effective quantity.

1. The Protein Component

The protein component comprises at least one protein selected from the group consisting of silk powder and keratin. These proteins have a strong resemblance in their chemical composition to that of the skin and hair. In addition, silk protein has an opposite electrostatic charge to that of skin and hair. This opposite electrostatic charge causes strong adhesion of the mascara to the eyelashes, which is crucial for the longer-lasting and water-resisting properties of the mascara of the present invention and which also contributes to a silky feel and appearance of the lashes.

Preferably, the protein component comprises both silk powder and keratin. Most preferably, these proteins are each present in a quantity of from about 0.5% to about 5% of the composition.

2. The Vegetable Wax Component

The vegetable wax component comprises at least one vegetable wax selected from the group consisting of jasmine wax and rose wax. These components provide flexibility to the film resulting from application of the mascara to the eyelashes, avoiding the usual brittleness associated with mascara and imparting smoothness, softness, and greatly improved flexibility. Preferably, the vegetable wax component comprises both jasmine wax and rose wax. Most preferably, both jasmine wax and rose wax are present in a quantity of from about 0.1% to about 0.3% of the composition.

3. The Vitamin Component

The vitamin component comprises at least one vitamin selected from the group consisting of fatty acid esters of ascorbic acid (Vitamin C) and their derivatives, tocopheryl esters (Vitamin E) and their derivatives, and panthenol and its derivatives. Panthenol is the racemic dl-form of 2,4,-dihydroxy-N-(3-hydroxypropyl)-3,3-dimethylbutanamide, and is also known as Vitamin $B_5$. The use of vitamins imparts a calming, soothing, and protective effect.

Preferably, the fatty acid esters of ascorbic acid are selected from the group consisting of ascorbyl palmitate, ascorbyl myristate, ascorbyl stearate, and mixtures thereof. Most preferably, the fatty acid ester of ascorbic acid is ascorbyl palmitate.

Preferably, the tocopheryl esters are selected from the group consisting of tocopheryl acetate, tocopheryl propionate, tocopheryl butyrate, and mixtures thereof. Most preferably, the tocopheryl ester is tocopheryl acetate.

Preferably, the vitamin component comprises ascorbyl palmitate, tocopheryl acetate, and panthenol. Most preferably, the ascorbyl palmitate comprises from about 0.05% to about 0.25% of the composition, the tocopheryl acetate comprises from abut 0.1% to about 0.3% of the composition, and the panthenol comprises from about 0.01% to about 0.25% of the composition. These vitamins exert a smoothing, calming anti-irritant effect on the eyes.

B. The Ancillary Components

The ancillary components, whose use is optional but preferable, impart desirable properties to the mascara composition of the present invention. These components can include (1) an antioxidant component; (2) a preservative component; (3) an emulsifier component; (4) a solvent component; (5) a thickener component; (6) a hydrophobic/waxy component; and (7) colorant. Most preferably, the composition of the present invention comprises all of these ancillary components, as indicated below.

1. The Antioxidant Component

The antioxidant component prevents oxidation of the ingredients of the composition. The antioxidant component can be a mixture of 70% propylene glycol, 20% propyl gallate, and 10% citric acid, and preferably comprises from about 0.05% to about 0.25% of the composition. A suitable mixture of propylene glycol, propyl gallate, and citric acid in these proportions is sold under the tradename of Tenox S-1™, manufactured by Eastman Kodak of Rochester, N.Y.

2. The Preservative Component

The preservative component is used to prevent the growth of microbes in the emulsified mascara composition, which is typically manufactured under clean, but non-sterile conditions. The preservative component is present in a quantity sufficient to prevent microbial growth in the composition, preferably a quantity such that the composition withstands the growth of bacteria from an experimental inoculation for at least three months.

Preferably, the preservative component comprises at least one of the following preservatives; Phenonip™, propylparaben, and sodium dehydroacetate. Phenonip™ is a practically colorless, viscous, liquid mixture of phenoxyethanol (60%–80%), methylparaben (13%–17%), ethylparaben (4%–6%), propylparaben (4%–6%), and butylparaben (4%–6%), and is available from Nipa Laboratories, Inc., Wilmington, Del.

Preferably, the preservative component comprises Phenonip™, propylparaben, and sodium dehydroacetate. Most preferably, the Phenonip™ comprises from about 0.4% to about 1.25% of the composition, the propylparaben comprises from about 0 02% to about 0.08% of the composition, and the sodium dehydroacetate comprises from about 0.01% to about 0.25% of the composition. In these figures, the proportion of propylparaben does not include any propylparaben contained in the Phenonip™.

3. The Emulsifier Component

Emulsifiers serve two functions. They act like a solubilizing agent to combine the water-soluble and non-water-soluble phases together; that is, to form a stable bridge between the waters and the oils of the ingredients. The emulsifiers also serve as a emollients, providing a pleasant, aesthetically appropriate tactile feeling when the emulsified composition is applied to the skin. The emulsifier component is present in a quantity sufficient to combine water-soluble and non-water-soluble phases of the composition.

Preferably, the emulsifier component comprises at least one emulsifier selected from the group consisting of triethanolamine and a glyceryl ester. The glyceryl ester is preferably selected from the group consisting of glyceryl stearate, glyceryl palmitate, glyceryl arachidate, and mixtures thereof. Most preferably, the glyceryl ester is glyceryl stearate.

Preferably, the emulsifier component comprises both glyceryl stearate and triethanolamine. Most preferably, the glyceryl stearate comprises from about 1% to about 4% of the composition and the triethanolamine comprises from about 2% to about 5% of the composition.

4. The Solvent Component

The composition can comprise a solvent component for greater uniformity and ease of preparation. The solvent component can be selected from the group consisting of ethylene glycol, propylene glycol, butylene glycol, and mixtures thereof. Preferably, the solvent component is propylene glycol. Most preferably, the propylene glycol comprises from about 0.4% to about 2.25% of the composition.

5. The Thickener Component

The composition can comprise a thickener component in a quantity sufficient to retain the composition when it is applied to the eyelashes of a wearer. The thickener component can comprise at least one thickener selected from the group consisting of acacia (also known as gum arabic) and hydroxyethylcellulose. Preferably, the thickener component comprises both acacia and hydroxyethylcellulose. Most preferably, the acacia comprises from about 3% to about 8% of the composition, and the hydroxyethylcellulose comprises from about 0.1% to about 2% of the composition.

6. The Hydrophobic/Waxy Component

The composition can further comprise a hydrophobic/waxy component. The hydrophobic/waxy component adds a smooth, attractive sheen to the eyelashes when the composition is applied. The hydrophobic/waxy component can comprise at least one ingredient selected from the group consisting of long-chain fatty acids, beeswax, carnauba, and paraffin. The long-chain fatty acids can be selected from the group consisting of palmitic acid, stearic acid, and arachidic acid. Preferably, the long-chain fatty acid is stearic acid.

Preferably, the hydrophobic/waxy component comprises all of stearic acid, beeswax, carnauba, and paraffin. Most preferably, the stearic acid comprises from about 3% to about 8% of the composition, the beeswax from about 4% to about 8% of the composition, the carnauba from about 1% to about 4% of the composition, and the paraffin from about 4% to about 10% of the composition.

7. The Colorant

The mascara composition can contain at least one colorant. Preferably, the composition contains from about 4% to about 8% of colorants. The colorants used are conventional cosmetic pigments chosen to impart the desired shade to the mascara. The use of colorants is well known in the cosmetic art.

The preferred concentrations of both the cosmetic components and the ancillary components are shown in Table I. Also shown in Table I are the mixtures of which each component is a part for the preparation of the composition as discussed below.

TABLE I

INGREDIENTS OF A PREFERRED MASCARA COMPOSITION OF THE PRESENT INVENTION

| Mixture | Component | Percentage Range |
|---|---|---|
| I* | Demineralized Water | 40.0–55.0 |
| I | Triethanolamine | 2.0–5.0 |
| I | Propylene Glycol | 0.4–2.25 |
| I | Phenonip | 0.4–1.25 |
| I | Sodium Dehydroacetate | 0.001–0.25 |
| I | Panthenol | 0.01–0.25 |
| II | Acacia | 3.0–8.0 |
| II | Hydroxyethylcellulose | 0.10–2.0 |
| III | Silk Powder | 0.50–5.0 |
| III | Colorants | 4.0–8.0 |

TABLE I-continued

INGREDIENTS OF A PREFERRED MASCARA
COMPOSITION OF THE PRESENT INVENTION

| Mixture | Component | Percentage Range |
|---|---|---|
| III | Keratin | 0.50–5.0 |
| III | Ascorbyl Palmitate | 0.05–0.25 |
| IV | Beeswax | 4.0–8.0 |
| IV | Stearic Acid | 3.0–8.0 |
| IV | Glyceryl Stearate | 1.0–4.0 |
| IV | Carnauba | 1.0–4.0 |
| IV | Paraffin | 4.0–10.0 |
| IV | Tenox S-1 ™ | 0.05–0.25 |
| IV | Propylparaben | 0.02–0.08 |
| IV | Tocopheryl Acetate | 0.1–0.3 |
| IV | Jasmine Wax | 0.1–3.0 |
| IV | Rose Wax | 0.1–3.0 |

*Water is split between Mixtures I and II in order to wet gums.

II. PREPARATION OF THE MASCARA COMPOSITION

The various mixtures and the sequences in which they are prepared and combined for the preparation of the mascara composition of the present invention are now described in some detail.

To the ingredients of Mixture II (acacia and hydroxyethylcellulose) is added a sufficient quantity of demineralized water to wet the gums in Mixture II. The ingredients of Mixture II plus the water are mixed with homogenization for one hour at 80° C. in a container, then allowed to stand overnight at room temperature in order to wet the gums.

Mixture II is then reheated and then Mixture I (triethanolamine, propylene glycol, Phenonip™, sodium dehydroacetate, and panthenol) is added, with mixing until the combination of Mixtures I and II is completely uniform with high-speed homogenization mixing. Mixture III (silk powder, colorants, keratin, and ascorbyl palmitate) is then added and the resulting combination mixed rapidly for one hour.

The temperature is brought to 85° C. The individual components of Mixture IV (beeswax, stearic acid, glyceryl stearate, carnauba, paraffin, Tenox S-1™, propylparaben, tocopheryl acetate, jasmine wax, and rose wax) are combined in a separate container and mixed until uniform at 85° C. Mixture IV is then added to the combination of Mixtures I, II, and III. The resulting combination is then mixed for one hour with rapid homogenization and then allowed to cool with slower mixing. Mixing is then terminated and the batch is "dropped" and allowed to solidify at 50° C.

ADVANTAGES OF THE INVENTION

The mascara composition of the present invention builds rapidly, smoothly, and evenly; the resulting film is longer lasting and pliable without brittleness or dryness. Due to the use of silk protein and keratin, the product produces thicker and longer lashes; in clinical tests, it was determined to increase lash thickness by 77% in one application and 178% in two. Due to the use of rose and jasmine waxes, the product is water-resistant, long-lasting, protective, and does not smudge or flake after application. It is easily removable with conventional eye makeup remover. It imparts a soothing, protective effect and does not cause allergic responses. It is particularly safe for contact lens wearers.

Although the present invention has been described in considerable detail with regard to certain preferred versions thereof, other versions are possible. Therefore, the spirit and scope of the appended claims should not be limited to the description of the preferred version contained herein.

What is claimed is:

1. An emulsified mascara composition comprising water and the following components which are emulsified and dispersed in the water:
    (a) a protein component comprising keratin and silk powder in substantially homogenized form, the keratin comprising from about 0.5% to about 5% of the composition and the silk powder comprising from about 0.5% to about 5% of the composition;
    (b) a vegetable wax component comprising rose wax and jasmine wax, the rose wax comprising from about 0.1% to about 3% of the composition and the jasmine wax comprising from about 0.1% to about 3% of the composition;
    (c) a vitamin component comprising ascorbyl palmitate, tocopheryl acetate, and panthenol, the ascorbyl palmitate comprising from about 0.05% to about 0.25% of the composition, the tocopheryl acetate comprising from about 0.1% to about 0.3% of the composition, and the panthenol comprising from about 0.01% to about 0.25% of the composition;
    (d) an anti-oxidant component in a quantity sufficient to retard oxidation of the composition;
    (e) a preservative component in a quantity sufficient to prevent microbial growth in the composition;
    (f) an emulsifier component in a quantity sufficient to combine water-soluble and non-water-soluble phases of the composition;
    (g) a solvent component;
    (h) a thickener component in a quantity sufficient to retain the composition on the eyelashes of a wearer when it is applied thereto;
    (i) a hydrophobic/waxy component; and
    (j) at least one colorant.

2. An emulsified mascara composition comprising: water, and emulsified and dispersed in the water:
    (a) about 2% to about 5% of triethanolamine;
    (b) about 0.4% to about 2.25% of propylene glycol;
    (c) about 0.4% to about 1.25% of a complex consisting essentially of phenoxyethanol, methylparaben, ethylparaben, propylparaben, and butylparaben;
    (d) about 0.01% to about 0.25% of sodium dehydroacetate;
    (e) about 0.01% to about 0.25% of panthenol;
    (f) about 3% to about 8% of acacia;
    (g) about 0.1% to about 2% of hydroxyethylcellulose;
    (h) about 0.5% to about 5% of silk powder in substantially homogenized form;
    (i) about 4% to about 8% of colorant;
    (j) about 0.5% to about 5% of keratin in substantially homogenized form;
    (k) about 0.5% to about 2.5% of ascorbyl palmitate;
    (l) about 4% to about 8% of beeswax;
    (m) about 3% to about 8% of stearic acid;
    (n) about 1% to about 4% of glyceryl stearate;
    (o) about 1% to about 4% of carnauba;
    (p) about 4% to about 10% of paraffin;
    (q) about 0.05% to about 0.25% of a mixture of 70% propylene glycol, 20% propyl gallate, and 10% citric acid;

(r) about 0.2% to about 0.8% of propylparaben;
(s) about 0.1% to about 0.3% of tocopheryl acetate;
(t) about 0.1% to about 3% of jasmine wax; and
(u) about 0.1% to about 3% of rose wax.

* * * * *